US012589244B2

(12) United States Patent
Iyer et al.

(10) Patent No.: US 12,589,244 B2
(45) Date of Patent: Mar. 31, 2026

(54) CERAMIC-TO-METAL JOINT FOR IMPLANTABLE PULSE GENERATORS

(71) Applicant: Medtronic, Inc., Minneapolis, MN (US)

(72) Inventors: Rajesh V. Iyer, Eden Prarie, MN (US); Steven T. Deininger, Plymouth, MN (US); Jenna N. George, Edina, MN (US); Andrew J. Thom, Maple Grove, MN (US); Brad C. Tischendorf, Minneapolis, MN (US); Gordon Munns, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 262 days.

(21) Appl. No.: 17/128,444

(22) Filed: Dec. 21, 2020

(65) Prior Publication Data

US 2021/0187291 A1 Jun. 24, 2021

Related U.S. Application Data

(60) Provisional application No. 62/952,976, filed on Dec. 23, 2019.

(51) Int. Cl.
*A61N 1/36* (2006.01)
*A61N 1/05* (2006.01)
(Continued)

(52) U.S. Cl.
CPC ......... *A61N 1/3605* (2013.01); *A61N 1/0551* (2013.01); *A61N 1/37229* (2013.01);
(Continued)

(58) Field of Classification Search
None
See application file for complete search history.

(56) References Cited

U.S. PATENT DOCUMENTS 5,470,345 A * 11/1995 Hassler .............. A61N 1/37512
257/E25.031
6,989,200 B2 1/2006 Byers et al.
(Continued)

FOREIGN PATENT DOCUMENTS

WO 2018208992 A1 † 11/2018

OTHER PUBLICATIONS

Mohammad S. Siddiqui et al., Vacuum Brazing of Alumina to Titanium for Implantable Feedthroughs Using Pure Gold as the Braze Metal, International Journal of Materials Science and Engineering, Jun. 2014, pp. 56-62, vol. 2, No. 1 (Year: 2014).*
(Continued)

*Primary Examiner* — Erica S Lee

(74) *Attorney, Agent, or Firm* — Husch Blackwell LLP

(57) ABSTRACT

An implantable pulse generator configured for delivering one or more electrical pulses to a target region within a body of a patient using an implantable neurostimulation lead, the implantable pulse generator comprising a hermetically sealed housing comprising a ceramic portion defining an inner volume configured to receive a charging coil assembly comprising a charging coil wrapped around an optional ferrite core material; an intermediate metal ring; and a case, wherein the intermediate metal ring comprises a first side joined to the ceramic portion by either a braze material or a diffusion bond, wherein the braze material or the diffusion bond is substantially free of nickel, and wherein the intermediate metal ring comprises a second side joined to the case portion.

15 Claims, 5 Drawing Sheets

(51) Int. Cl.

| | |
|---|---|
| *A61N 1/372* | (2006.01) |
| *A61N 1/375* | (2006.01) |
| *A61N 1/378* | (2006.01) |
| *B23K 1/00* | (2006.01) |
| *B23K 26/324* | (2014.01) |
| *B23K 101/36* | (2006.01) |
| *B23K 103/00* | (2006.01) |
| *B23K 103/18* | (2006.01) |
| *B23K 20/02* | (2006.01) |

(52) U.S. Cl.
CPC ........... *A61N 1/375* (2013.01); *A61N 1/3754* (2013.01); *A61N 1/3756* (2013.01); *A61N 1/3787* (2013.01); *B23K 1/0016* (2013.01); *B23K 20/02* (2013.01); *B23K 26/324* (2013.01); *B23K 2101/36* (2018.08); *B23K 2103/18* (2018.08); *B23K 2103/52* (2018.08)

(56) References Cited

U.S. PATENT DOCUMENTS

| | | | | |
|---|---|---|---|---|
| 8,162,684 | B1 * | 4/2012 | Sochor ................. | H01R 13/639 |
| | | | | 439/289 |
| 8,329,314 | B1 * | 12/2012 | Xiaohai ................ | A61L 31/022 |
| | | | | 228/248.1 |
| 8,467,875 | B2 | 6/2013 | Bennett et al. | |
| 9,446,235 | B2 | 9/2016 | Su et al. | |
| 9,700,731 | B2 † | 7/2017 | Nassif | |
| 9,981,122 | B2 † | 5/2018 | Rawat | |
| 10,201,702 | B2 | 2/2019 | Bonde et al. | |
| 2007/0270916 | A1 * | 11/2007 | Fischell ................... | A61N 1/37 |
| | | | | 607/36 |
| 2008/0103556 | A1 * | 5/2008 | Li ......................... | A61L 31/022 |
| | | | | 607/33 |

| | | | | |
|---|---|---|---|---|
| 2009/0171420 | A1 * | 7/2009 | Brown ................. | A61N 1/3787 |
| | | | | 607/116 |
| 2012/0265003 | A1 * | 10/2012 | D'Ambrosio ....... | A61M 60/875 |
| | | | | 600/16 |
| 2016/0199658 | A1 * | 7/2016 | Nassif .................... | H01Q 7/005 |
| | | | | 29/601 |
| 2016/0331978 | A1 * | 11/2016 | Tischendorf ....... | A61N 1/36071 |
| 2017/0018811 | A1 * | 1/2017 | Bradwell ............ | H01M 50/463 |
| 2017/0143959 | A1 * | 5/2017 | Boling ................. | A61N 1/3754 |
| 2019/0290911 | A1 * | 9/2019 | Whitehead ........... | A61B 5/0031 |
| 2019/0374776 | A1 * | 12/2019 | Mishra ................. | A61N 1/3752 |
| 2020/0001093 | A1 * | 1/2020 | Thom ..................... | H04B 5/24 |
| 2020/0295406 | A1 * | 9/2020 | Hovland .............. | H01M 50/119 |
| 2020/0306528 | A1 * | 10/2020 | Linden .................... | A61N 1/05 |

OTHER PUBLICATIONS

Srinidhi Nagaraja et al., Current practices in corrosion, surface characterization and nickel leach testing of cardiovascular metallic implants, J Biomed Mater Res B Appl Biomater, Aug. 2017, pp. 1330-1341 (Year: 2017).*

Hong Bian et al., Microstructure Evolution and Mechanical Properties of Titanium/Alumina Brazed joints for Medical Implants, Metals, Jun. 2019, vol. 9, Issue 6.†

Srinidhi Nagaraja et al., Current practices in corrosion, surface characterization, and nickel leach testing of cardiovascular metallic implants, J Biomed Mater Res B Appl Biomater, Aug. 2017, pp. 1,330-1,341.†

Mohammad S. Siddiqui et al., Vacuum Brazing of Alumina to Titanium for Implantable Feedthroughs Using Pure Gold as the Braze Metal, International Journal of Materials Science and Engineering, Jun. 2014, pp. 56-62, vol. 2, No. 1.†

\* cited by examiner
† cited by third party

CERAMIC-TO-METAL JOINT FOR IMPLANTABLE PULSE GENERATORS

CROSS-REFERENCE TO RELATED APPLICATIONS

This application claims the benefit of U.S. Provisional Application No. 62/952,976 filed on Dec. 23, 2019, the entirety of which is incorporated herein by reference.

FIELD

The present technology is generally related to implantable pulse generators for neuromodulation or similar devices and the construction of such systems.

BACKGROUND

Treatments using neurostimulation systems have become increasingly common in recent years. Neurostimulation (also referred to as neuromodulation) has been used to treat a variety of ailments and associated symptoms including acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement disorders include muscle paralysis, tremor, dystonia and Parkinson's disease. Affective disorders include depressions, obsessive-compulsive disorder, cluster headache, Tourette syndrome and certain types of chronic pain. Bladder related dysfunctions include overactive bladder ("OAB"), urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory or motor control associated with that condition or associated symptoms.

SUMMARY

The present disclosure generally relates to implantable medical devices ("IMD") and, more specifically, to an implantable pulse generator ("IPG"). During normal operation, IPGs generate a series of electrical pulses as part of a neurostimulation treatment regimen. Within certain IPGs depending on the materials used in their construciton, unintended nickel leaching may occur during normal device operation. In some instances, the source of such nickel leaching may be the braze materials conventionally used in IMDs to join metal and ceramic housing components together. The present disclosure provides alternative techniques for coupling together ceramic and metal housing materials of IMDs, in particular IPGs, to eliminate or reduce nickel leaching while also providing a hermetic seal between ceramic and metal components.

In one aspect, the present disclosure provides an implantable pulse generator configured for delivering one or more electrical pulses to a target region within a body of a patient using an implantable neurostimulation lead including a plurality of neurostimulation electrodes electrically coupleable to the device. The implantable pulse generator includes a hermetically sealed housing that includes a) a ceramic portion including a ceramic material, the ceramic portion defining a first inner volume, b) a case portion defining a second inner volume, c) an intermediate metal ring positioned between the ceramic portion and the metal case portion, the intermediate metal ring having a first side joined to the ceramic portion by either a braze material or a diffusion bond and a second side joined to the case portion, where the braze material or the diffusion bond is substantially free of nickel, d) a header portion configured to electrically couple to the implantable neurostimulation lead, the header portion including a feed through assembly that connects the header portion to the case portion, the feed through assembly electrically coupling components of the header portion and implantable neurostimulation lead to circuitry positioned within the second inner volume defined by the case portion, and e) a charging coil assembly including a charging coil wrapped around an optional ferrite core material, the charging coil assembly is at least partially housed within the first inner volume defined by the ceramic portion, where the charging coil assembly is configured to wirelessly communicate with an external charging device across the ceramic portion to charge a battery positioned within the implantable pulse generator.

In another aspect, the disclosure provides a method of assembling an implantable pulse generator or portion thereof configured to deliver one or more electrical pulses to a target region within a body of a patient using an implantable neurostimulation lead. The method including forming a ceramic portion including a ceramic material, the ceramic portion defining a first inner volume; aligning the ceramic portion adjacent to a first side of an intermediate metal ring and joining the ceramic portion to the first side of the intermediate metal ring by brazing or diffusion bonding, where the braze material or the diffusion bond is substantially free of nickel and forms a hermetic seal between joined portions of the ceramic portion and the intermediate metal ring; and joining a second side of the intermediate metal ring to a case portion including metal or ceramic material, where joined portions of the case portion and the intermediate metal ring form a hermetic seal.

In another aspect, the disclosure provides an implantable neurostimulator device configured for delivering one or more electrical pulses to a target region within a body of a patient using an implantable neurostimulation lead including a plurality of neurostimulation electrodes electrically coupleable to the device, the implantable neurostimulator device including a) a ceramic portion including a ceramic material and forming part of a housing of the implantable neurostimulator device, where the ceramic portion defines a first inner volume, b) a metal case portion forming part of the housing of the implantable neurostimulator device, where the metal case portion defines a second inner volume, c) an intermediate metal ring positioned between the ceramic portion and the metal case portion and forming part of the housing of the implantable neurostimulator device, where the intermediate metal ring includes a first side joined to the ceramic portion by either a braze material or a diffusion bond, where the braze material and the diffusion bond are substantially free of nickel, the intermediate metal ring having a second side joined to the metal case portion by a laser-weld joint, where the ceramic portion, metal case portion, and intermediate metal ring collectively define a third internal volume of the housing, d) a header portion configured to electrically couple to the implantable neurostimulation lead, where the header portion includes a multi-pin feed-through assembly including a metallic base plate, where the metallic base plate of the multi-pin feed-through assembly is laser-welded to the metal case portion to provide a hermetic seal between the header portion and the metal case portion, where the multi-pin feed-through electrically couples components of the header portion and implantable neurostimulation lead to electronic circuitry at least partially positioned within the second inner volume defined by the metal case portion, and e) electronic circuitry disposed within the third internal volume of the housing, where the circuitry is configured to generate the one or more electrical pulses delivered to the target region within a body of a patient using the implantable neurostimulation lead. The electronic circuitry includes a printed circuit board being at least partially housed within the second inner volume defined by the metal case portion, the printed circuit board having a rechargeable battery and a temperature sensor electrically coupled thereto, where the temperature sensor is configured to detect a temperature of a portion the implantable neurostimulator device during at least one of a recharge cycle of implantable neurostimulator device or during the delivery of one or more electrical pulses to a target region within a body of a patient using an implantable neurostimulation lead; and a charging coil assembly including a charging coil defining a central coil axis and a ferrite core material, where the charging coil of the charging coil assembly is wrapped around a ferrite core material such that the ferrite core material is aligned with the central coil axis, where the charging coil assembly is housed within the first inner volume defined by the ceramic portion so that the central coil axis is substantially perpendicular to a normal defined by a major plane of the implantable neurostimulator device, and where the charging coil assembly is configured to wirelessly communicate with an external charging device across the ceramic portion to charge the rechargeable battery positioned within the implantable neurostimulator device. The implantable neurostimulator device is hermetically sealed and defines a total device volume of less than 10 cubic centimeters, and where the implantable neurostimulator device is configured to be fully implanted within a body of a patient and adapted for sacral nerve stimulation treatment.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
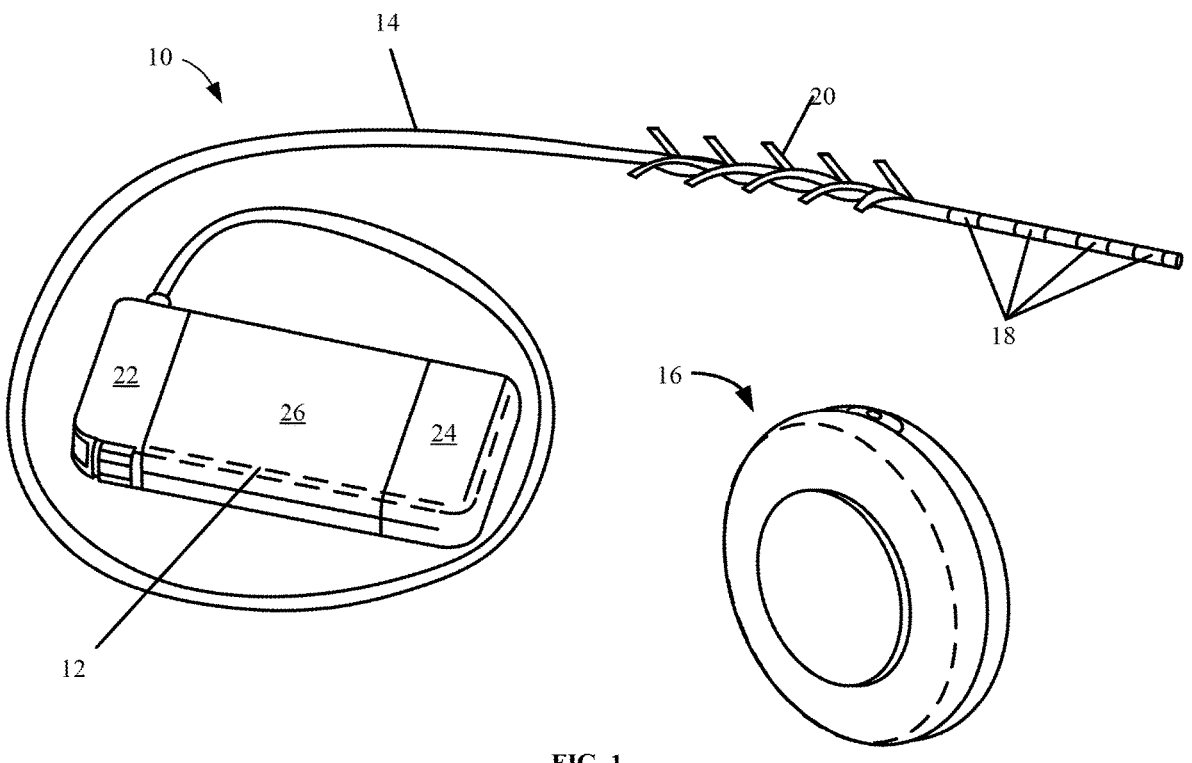
FIG. 1 is a schematic illustration of an exemplary nerve stimulation system that includes a fully implantable IPG adapted for sacral nerve stimulation treatment.

Neurostimulation has been particularly suited for treatment of several medical ailments including urinary and fecal dysfunctions. OAB is one of the most common urinary dysfunctions and historically has been under-recognized and significantly underserved by the medical community. OAB is a complex condition characterized by the presence of bothersome urinary symptoms, including urgency, frequency, nocturia and urge incontinence. Current estimates indicate that about 33 million Americans suffer from OAB including about 30% of all men and 40% of all women. OAB symptoms can have an impact on patient psychosocial functioning and quality of life. Furthermore, OAB can impose significant financial burden on individuals, their families, and healthcare organizations. Chronic constipation, fecal incontinence, and overlapping chronic constipation occur more frequently in patients with OAB. The prevalence of co-morbid conditions is also significantly higher for patients with OAB than in the general population including, for example, falls and fractures, urinary tract infections, skin infections, vulvovaginitis, cardiovascular, and central nervous system pathologies.

Conventional OAB treatments generally include lifestyle modifications such as changes in diet, healthy habits, and the like. An additional approach is to treat the condition using medication or injection. Typically, after such approaches have proven ineffective, neuromodulation involving neurostimulation of nerves relating to the urinary systems such as Percutaneous Tibial Nerve Stimulation (PTNS) and Sacral Nerve Stimulation (SNM) is considered.

Neurostimulation systems typically make use of an array of neurostimulation electrodes to treat one or more target nerve structures. The electrodes are often mounted together on a multi-electrode lead, and the lead implanted in tissue of the patient at a position that is intended to result in electrical coupling of the electrode to the target nerve structure (e.g., the sacral nerve), typically with at least a portion of the coupling being provided via intermediate tissues. Other approaches may also be employed, for example, with one or more electrodes attached to the skin overlying the target nerve structures, implanted in cuffs around a target nerve, or the like.

One approach to delivering neurostimulation involves implanting the entire neurostimulation system within the body of a patient. Such neurostimulation devices, generally referred to as implantable medical devices (IMB) or implantable neurostimulators can be surgically implanted within a patient and tailored to stimulate a target nerve site. Even in patients where implantation of such neurostimulation systems has proven effective, frequent adjustments and changes to the stimulation protocol may be needed to develop an appropriate treatment program.

IMDs include their own power source, which can include chargeable or non-chargeable devices. The lifetime and battery life of non-chargeable IMDs may be relatively short requiring routine replacement every few years. Rechargeable IMDs offer extended life for the IMB but provide their own challenges for creating an effective recharge system in a device having limited space. Further, as the device size is reduced, effective means of creating a device that is hermetically sealed and provides the necessary means of electrical function is needed.

The present disclosure generally relates to implantable neurostimulators, and, more specifically, to a rechargeable implantable pulse generator (IPG). The IPGs are configured to deliver one or more electrical pulses to a target region (e.g., sacral nerve) within a patient's body. FIG. 1 schematically illustrates an exemplary nerve stimulation system 10 that is fully implantable and adapted for sacral nerve stimulation treatment. Nerve stimulation system 10 includes an IPG 12, neurostimulation lead 14 coupled to IPG 12, and external charging device 16. Neurostimulation lead 14 has a proximal end electrically coupled to IPG 12 and a distal end that includes a plurality of neurostimulation electrodes 18 that deliver electrical stimulation to the patient using an appropriate stimulation technique such as those described further below. Optionally, lead 14 may include a tined anchor portion 20 that helps maintain the position of neurostimulation electrodes 18 along a targeted treatment site or nerve within the patient. Lead 14 may further include one or more radiopaque markers to assist in locating and positioning the distal end of the lead using visualization techniques such as fluoroscopy. In some embodiments, IPG 12 is configured to provide monopolar or bipolar electrical pulses that are delivered to the targeted nerves through one or more neurostimulation electrodes 18.

In preferred embodiments, nerve stimulation system 10 is configured for sacral neuromodulation ("SNM"). SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. In sacral nerve stimulation, neurostimulation electrodes 18 are placed next to a sacral nerve, usually at the S3 level, by inserting the lead 14 into the corresponding foramen of the sacrum, e.g., through the third sacral (S3) foramen. Lead 14 is subsequently attached to IPG 12. The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

Although nerve stimulation system 10 is primarily described for placement and use in delivering sacral nerve stimulation, in other embodiments, delivery of stimulation to the pudendal nerve of a patient may more specifically target the pelvic floor muscles of the patient. For example, in some examples, stimulation of the S3 sacral nerve may activate one or more leg muscles of the patient, in addition to activating one or more pelvic floor muscles. Activation of the one or more leg muscles may be unnecessary and unwanted in treatment for strengthening the pelvic floor muscles of the patient. In some examples, stimulation of the pudendal nerve can more specifically target pelvic floor muscles, e.g., the external urethral sphincter, without activating one or more leg muscles. SNM may be used to treat patients suffering from any number of pelvic floor disorders such as pain, urinary incontinence, fecal incontinence, sexual dysfunction, or other disorders treatable by targeting one or more sacral nerves. Additionally, while IPG 12 is discussed in the context of treating pelvic disorders, the techniques and designs disclosed herein may be applicable to other types of IMDs used for treating other types of disorders. For example, IPG 12 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other embodiments, lead 14 may provide one or more sensors configured to allow IPG 12 to monitor one or more parameters of the patient. The one or more sensors may be provided in addition to, or in place of, therapy delivery by lead 14. Examples of additional stimulation therapy applications and stimulation parameters can be found in for example, U.S. Pat. No. 10,201,702 B2 by Bonde et al., U.S. Pat. No. 8,467,875 B2 by Bennett et al., and U.S. Pat. No. 9,446,235 B2 by Su et al., each of which is incorporated by reference in its entirety.

Figure 2A:
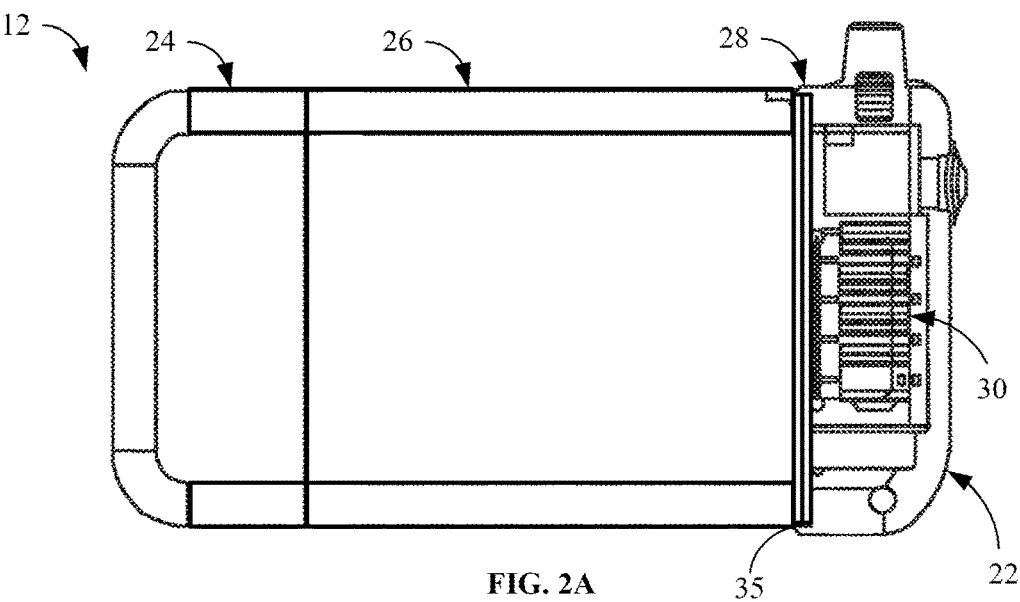
FIGS. 2A-2C are schematic illustrations showing various portions of the FIG. 1 IPG.
Figure 2B:
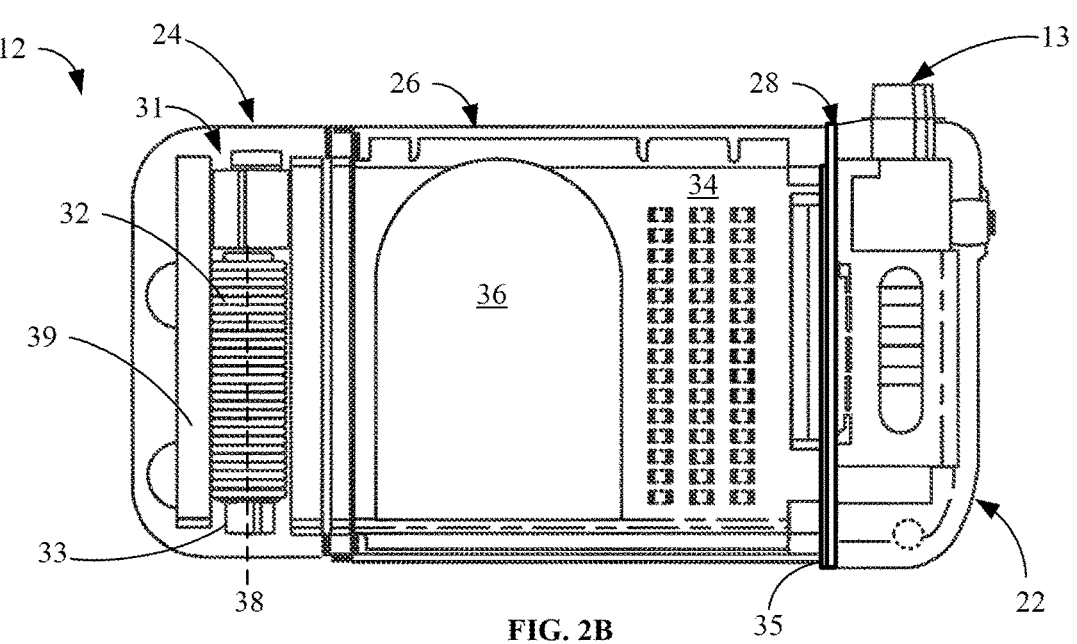

FIGS. 2A-2B are schematic illustrations showing various portions of IPG 12. As shown in FIGS. 2A-2B, IPG 12 may include a header portion 22 at one end and a ceramic portion 24 at the opposite end with a case portion 26 in between. The header portion 22 includes a feed through assembly 28 and connector stack 30. Ceramic portion 24 at least partially houses charging coil assembly 31 that facilitates wireless charging between charging coil 32 and external charging device 16. Ceramic portion 24 may also contain antenna 39. Charging coil assembly 31 or antenna 39 may be used to facilitate wireless communication with a clinician programmer, a patient remote, other devices and the like. Spanning between ceramic portion 24 and header portion 22 is case portion 26, which encases at least a portion of the printed circuit board 34, battery 36, memory and controller components that facilitate the electrical pulse programs described herein, and other circuitry components and operation modules of IPG 12. Case portion 26 may be formed using biocompatible metal or ceramic material. In preferred embodiments, case portion 26 may be formed of high grade titanium alloy (e.g., Grade 5 Titanium alloy, which includes approximately 6% aluminum and 4% vanadium and is commonly known as Ti 6Al-4V.) having high corrosion resistance and excellent biocompatibility. Forming case portion 26 of high grade titanium can also help shield and protect the sensitive internal circuitry on circuit board 34 as well as help reduce the overall size of IPG 12 leading to a less intrusive device.

Ceramic portion 24, and in some examples case portion 26, may be formed using a biocompatible ceramic material including, but not limited to, zirconia or alumina based ceramics. Such ceramics may be doped or stabilized with additional components. For example, in some embodiments, the ceramic may be yttria stabilized zirconia such as 3Y-TZP ceramic (e.g., 3 mol percent yttria-stabilized tetragonal zirconia polycrystals), which has a high flexural strength and impact resistance and has been commercially utilized in a number of implantable medical technologies. It will be appreciated, however, that other ceramics or other suitable materials may be used for construction of housing portions of IPG 12, and that ceramic may be used to form additional portions of the housing.

As shown in FIG. 2B, ceramic portion 24 defines an internal volume (e.g., cavity) that at least partially houses charging coil 32 and optional antenna 39 (e.g., RF antenna). In contrast with other materials (e.g., metals), the ceramic encasement may help reduce interference or unintended electrical shielding between charging coil 32 and antenna 39 and other wireless devices configured to communicate with IPG 12 including, but not limited to, external charging device 16 during a recharge cycle, external programming, or remote devices. Utilization of ceramic material provides an efficient, radio-frequency-transparent window for wireless communication with the external patient remote, charging device, programmer. This ceramic window provided by ceramic portion 24 may also facilitate miniaturization of the implant by reducing the size of the needed charging coil 32 while maintaining an efficient, radio-frequency-transparent window for long term and reliable wireless communication between IPG 12 and external controllers or devices. Additionally, or alternatively, the ceramic portion exhibits less thermal heating during recharge compared to a metal counterpart material. This in turn may allow for higher recharge power to be delivered to IPG 12 and lower the total time for a recharge cycle.

The IPG's wireless communication is generally stable over the lifetime of the device, unlike prior art products where the communication antenna is placed in the header or outside the hermetic case. The communication reliability of such prior art devices may be reduced due to the change in dielectric constant of the header material in the human body over time. Thus, housing charging coil 32 and optional antenna 39 within ceramic portion 24 may provide a more durable configuration. In preferred embodiments, the entire charging coil 32 and antenna 39 (e.g., apart from electrical leads connecting the such parts to circuit board 34 or other components) are housed within the inner volume defined by ceramic portion 24. Battery 36 and the majority of circuit board 34 and other sensitive components attached thereto may be housed within a volume defined by case portion 26 or other parts of IPG 12 to help shield such components from outside electrical sources.

Charging coil 32 may include a wire coil (e.g., single or multi-pass wound coil) wrapped around an optional ferrite core material 33. Optional ferrite core 33 and charging coil 32 may be considered part of the charging coil assembly 31, which is at least partially housed, more preferably fully housed, in ceramic portion 24. Ferrite core 33, if included, can help concentrate the magnetic field flux through the ceramic portion 24 as opposed to the case portion 26. This configuration helps maximize coupling efficiency, which reduces the required magnetic field and in turn reduces device heating during charging. In particular, because the magnetic field flux is oriented in a direction perpendicular to the smallest metallic cross section area, heating during charging is minimized. This configuration also allows IPG 12 to be effectively charged at depth of about 3 cm with external charging device 16, when positioned on a skin surface of the patient near IPG 12 and reduces re-charging time. Ferrite core 33 may help redirect or focus the magnetic field lines generated by the charging coil within the external charging device 16 towards the charging coil 32 so that the system is less susceptible to misalignment between the recharge coils.

Figure 3:
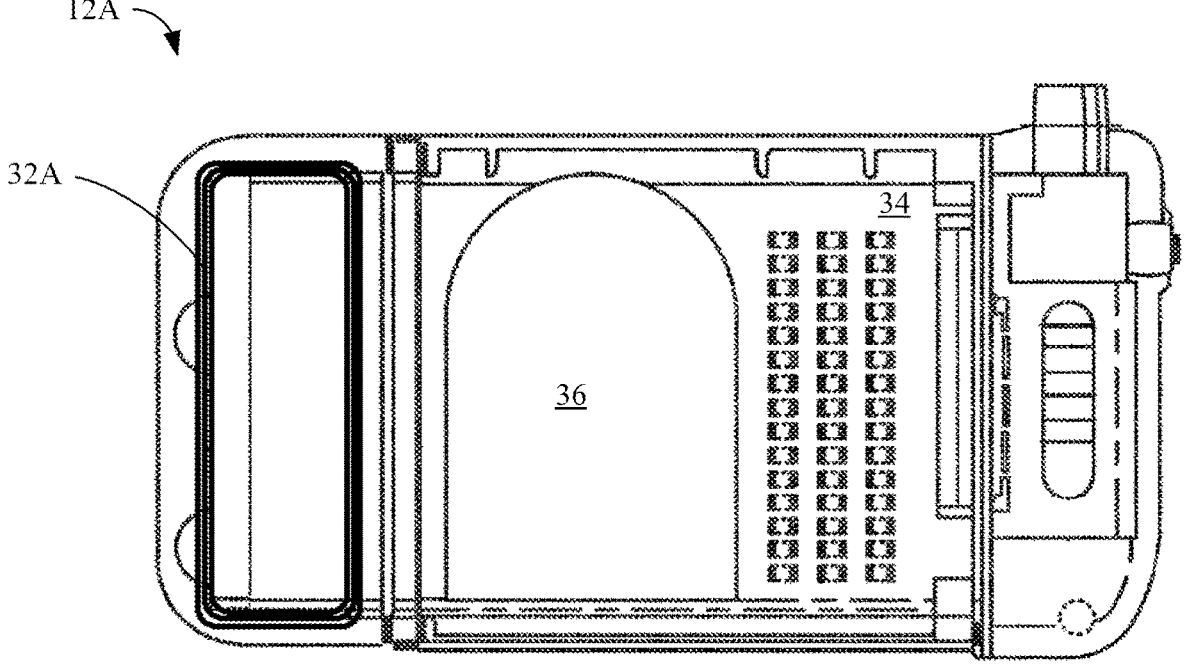
FIG. 3 is a schematic illustration showing part of an IPG.

In some embodiments, charging coil 32 may be aligned within IPG 12 such that the central axis 38 of the coil (e.g., axis by which the wire is wrapped around) aligns substantially perpendicular (e.g., perpendicular or nearly perpendicular) to a normal defined by the major plane of IPG 12 (e.g., perpendicular to the normal of the largest surface of IPG 12) as shown in FIG. 2B. Such an orientation may help maximize recharge functions of IPG 12 provided proper alignment between charging coil 32 and the primary coil of external charging device 16 is maintained. FIG. 3 shows an example IPG 12A similar to that of FIG. 2B having an alternative coil orientation. Within IPG 12A, charging coil 32A has a coil axis that aligns substantially parallel (e.g., parallel or nearly parallel) to a normal defined by the major plane of IPG 12A, both of which extend out of the page. In this manner, the aperture size of charging coil 32A may be substantially increased to help increase the coupling between charging coil 32A and external charging device 16. Having a larger aperture size may help reduce misalignments between charging coil 32A and external charging device 16. In some embodiments, charging coil 32A may be sized to conform to the inner perimeter defined by the inner volume of ceramic portion 24. This may help to maximize the length of each coil wrapping and aperture size of charging coil 32A. Charging coil 32A may be at least partially contained, and preferably, fully contained within ceramic portion 24. In embodiments where case portion 26 is formed from ceramic material, charging coil 32A may extend into the inner volume defined by case portion 26 to increase the relative aperture size of the coil. For example, the charging coil may be extended around the perimeter of circuit board 34.

In addition to communicating with external charging device 16, charging coil 32 or antenna 39 may as mentioned above also be used to communicate wirelessly with an external programmer, patient remote, or other device. The external programmer or patient remote may be used to operate IPG 12 to deliver stimulation therapy, modify therapy parameters, communicate information regarding the status of IPG 12 or the patient, or the like. The clinician programmer can include specialized software, specialized hardware, or both, to aid in lead placement, programming, re-programming, stimulation control, or parameter setting. In addition, IPG 12 can allow the patient at least some control over stimulation (e.g., initiating a pre-set program, increasing or decreasing stimulation), or to monitor battery status with the patient remote.

Due to IPG 12 being implanted within the body of the patient, it is desirable to have the internal components of IPG 12 be hermetically sealed. However, bonding between the ceramic material of ceramic portion 24 and case portion 26 or case portion 26 and header 22 poses several challenges. This can be particularly challenging when case portion 26 is made from high grade titanium alloy (e.g., Grade 5 Titanium). A conventional approach to address this problem has been to use a titanium-nickel alloy interlayer to braze bond the two components together. For example, the ceramic portion 24 and case portion 26 (e.g., Grade 5 Titanium) are positioned adjacent to one another with an interlayer collar positioned therebetween of a compatible nickel-titanium alloy (e.g. 50-67% titanium). The three components may be pressed together under vacuum and heated to above the softening point of the nickel-titanium alloy to braze the interlayer collar to the ceramic and titanium case portions 24 and 26 respectively. U.S. Pat. No. 6,989,200 B2 by Byers et al. discloses ceramic to titanium brazing techniques using nickel-titanium alloy. Nickel-titanium alloy brazing, such as that described in U.S. Pat. No. 6,989,200 B2, has been used to create a hermetic seal between ceramic and titanium metal portions for various IMDs.

Surprisingly, in certain IPG devices, complications have been observed during operation of the IPG with nickel being leached from the device. It is believed the nickel-titanium alloy braze used in these IPGs may be the source for the nickel leaching despite the nickel-titanium braze material being used in other IMDs. While the reason for the nickel leaching is not fully understood, one theorized reason for the nickel leaching is that the resultant braze joint of these devices is non-homogeneous and the pulse generation within the IPGs may cause some of the nickel content in the braze joint to leach from the device. Other reasons may also exist.

At sufficiently high doses, nickel leaching may produce adverse effects at the site of implantation or other sites within the patient. This phenomenon appears to be associated primarily with certain types of IPG devices. Indeed, Nitinol, a particular nickel-titanium alloy with advantageous shape memory properties, has long been used in IMDs and other medical devices without evident nickel leaching.

Figure 4A:
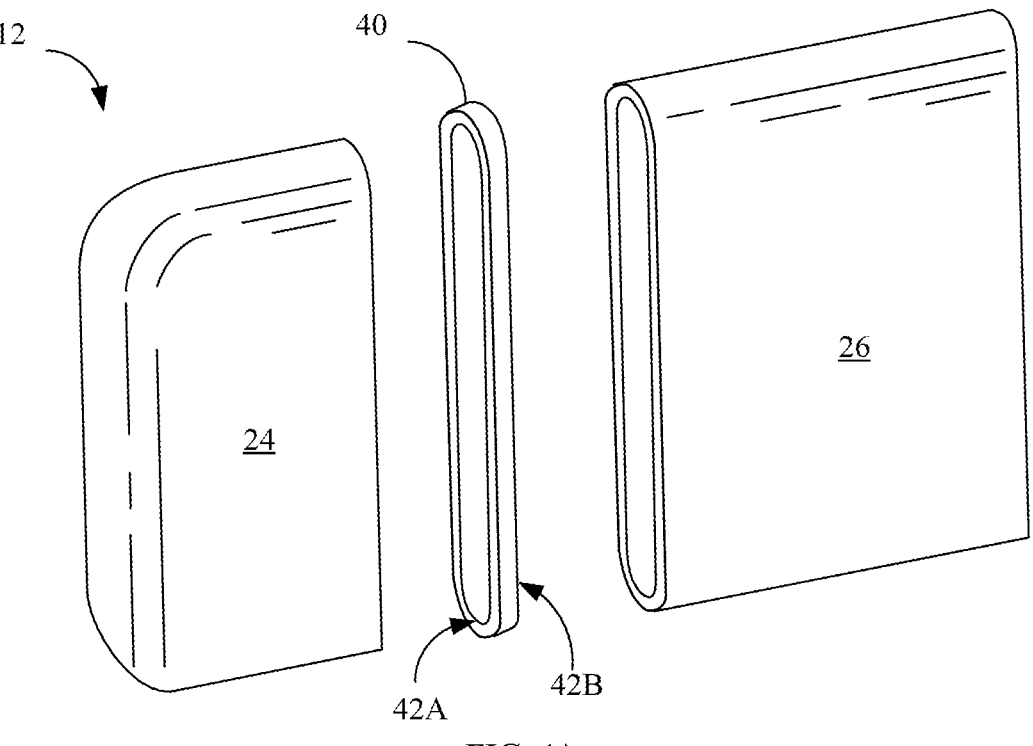
FIG. 4A is an exploded schematic view of the FIG. 1 IPG including a ceramic portion and a case portion with an intermediate metal ring positioned therebetween.
Figure 4B:
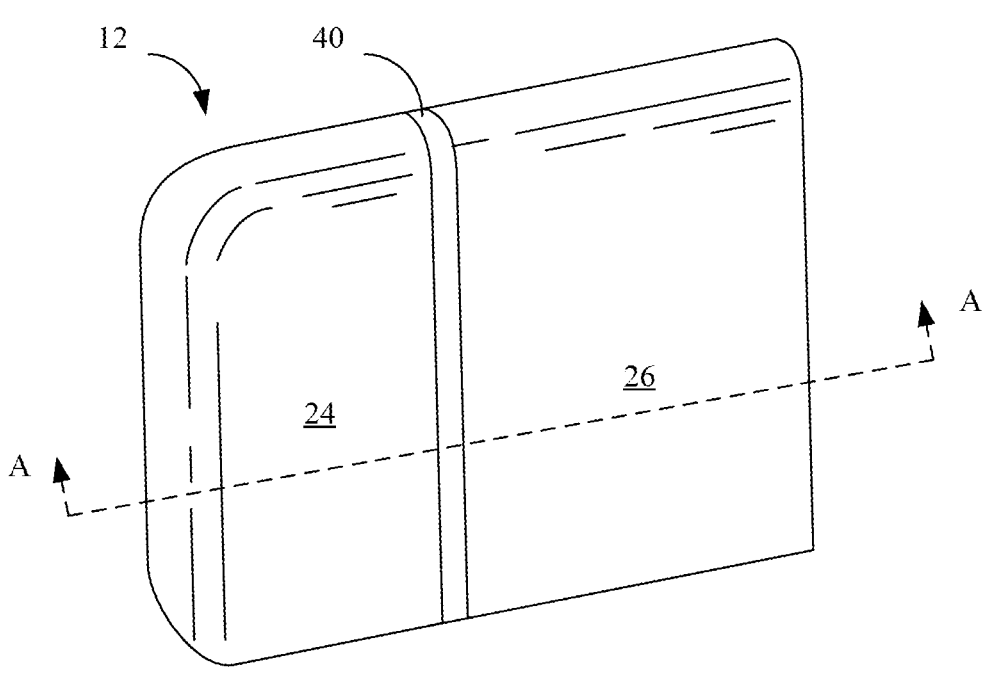
FIG. 4B is a perspective schematic view of the FIG. 1 IPG including a ceramic portion and a case portion with an intermediate metal ring positioned therebetween.

To address the problems associated with nickel leaching, the disclosed IPG employs an alternative bonding technique between ceramic and metal case portions 24 and 26. FIGS. 4A and 4B are schematic exploded and assembled views respectively of IPG 12 including ceramic and case portions 24 and 26 with an intermediate metal ring 40 positioned therebetween. Intermediate metal ring 40 includes a first side 42A that can be brazed or diffusion bonded to ceramic portion 24 using a biocompatible material substantially free of nickel, and a second side 42B that can be joined to case portion 26 by, for example, laser welding to provide an effective hermetic seal between case portion 26 and ceramic portion 24.

Intermediate metal ring 40 can provide several advantages in terms of assembly and biocompatibility. For example, intermediate metal ring 40 may be composed of a different metal or alloy than case portion 26 that is more compatibly joined to ceramic portion 24 by braze or diffusion bonding. Additionally, intermediate metal ring 40 can be joined to metal case portion 24 by, for example, laser welding at a later part in the assembly process. In this manner, ceramic portion 24 and metal ring 40 can be joined using high temperature braze or diffusion bonding techniques prior to assembly of the inner components of IPG 12 (e.g., charging coil 32, battery 36, and circuit board 34). The components can then be assembled within ceramic and case portion 24 and 26 and metal ring 40 can be laser welded to case portion 26, which typically involves localized heating of the two components and is less potentially damaging to the sensitive inner electronics. Further, laser welding helps reduce the thermal strain on case portion 26 and preserve its underlying microstructure, which does not get heated to high braze temperatures.

Intermediate metal ring 40 may include a metal or alloy that is compatible with substantially nickel free braze materials or diffusion bonding materials. Such metals may include titanium and titanium alloys such as Grade 1-5 Titanium, with Grade 1-4 Titanium being preferred. While Grade 1-5 Titanium is compatible with many braze materials including gold, Grade 5 Titanium causes alternative braze materials such as gold to overwet the titanium resulting in fillets and an insufficient braze joint being formed. Grades 1-4 Titanium provide better compatibility with alternative braze materials like gold without the drawbacks of overwetting. Grade 5 Titanium has advantages as a case material including, for example, good biocompatibility, good electrical resistances which can help reduce eddy current losses in IPG 12, and the like. As such, in some embodiments, intermediate metal ring 40 and case portion 26 may each comprise different materials such as different titanium alloy grades. More preferably, case portion 26 may include Grade 5 Titanium while intermediate metal ring 40 includes Grade 1-4 Titanium.

In some embodiments, intermediate metal ring 40 is brazed to ceramic portion 24. In such examples, the braze material used to join first side 42A of intermediate metal ring 40 to ceramic portion 24 may be a noble metal or alloy, preferably gold, that is substantially free of nickel (e.g., contains less than 5 wt. % nickel, more preferably less than 1 wt. %). Gold has a proven record of being biocompatible with patient tissue in a variety of IMDs and thus avoids the complications associated with using a nickel based material. Other braze materials may include, but are not limited to, high purity gold, and gold alloys containing silver, copper, tin, or zinc without departing from the spirit and scope of the present teachings. In some embodiments, the braze material may be an active gold braze alloyed with titanium such as APA 10b (96% Au with 5% Ti) or APA 10c (98% Au with 2% Ti). In some embodiments, the braze material can be reinforced with oxide, carbide, or nitride particles of refractory metals such as molybdenum, tungsten, hafnium, niobium, or zirconium.

To facilitate brazing, the ceramic portion 24 and first side 42A of intermediate metal ring 40 may be brought in proximity to one another with a braze material 48 (FIG. 5) disposed in between. In some embodiments, ceramic portion 24 and intermediate metal ring 40 may be gapped at a set distance to accommodate an appropriate amount of braze material 48. If the gap volume is too small, excess braze in the form of braze fillets may be formed and the gold braze may spill. If too large, a convex shaped braze fillet may exert a strong tensile loading and promote delamination of braze or may lead to pockets in the resultant braze joint. In preferred embodiments, the gap separating ceramic portion 24 and intermediate metal ring 40 may be about 10 μm to about 50 μm.

Braze material 48 may be initially applied in any suitable form. For example, braze material 48 may be initially deposited between the ceramic portion 24 and intermediate metal ring 40 as a prefabricated or machined ring, a paste or powder, one or more foil layers, an alloy laminate, or the like. Braze material 48 by be positioned between the ceramic portion 24 and metal ring 40 and the system heated to the desired temperature to cause the braze material to alloy and bond with the adjacent components.

In some embodiments, to improve bonding between intermediate metal ring 40 and ceramic portion 24, a braze wetting agent may be used on ceramic portion 24 to promote the distribution of braze material 48. A preferred braze wetting agent that is particularly suited for gold includes niobium metal which can be sputtered onto ceramic portion 24. During the brazing process, alloying takes place between the niobium sputter, gold in braze material 48, and metal (e.g., titanium) of intermediate metal ring 40. The concentration of niobium and titanium in the resultant alloy may depend on the temperature schedule during brazing and on the gap distance between the components. For example, during brazing, titanium and gold form a series of intermetallic compounds, and a gold mixed crystal phase field showing solid state (ss) solubility of roughly up to 6 mass % titanium.

In other embodiments, intermediate metal ring 40 is diffusion bonded to ceramic portion 24. A "diffusion bond" refers to technique of bonding materials in the solid state to form a monolithic joint through the formation of bonds at an atomic level, as a result of closure of the mating surfaces due to the local plastic deformation at elevated pressure and temperature which aids interdiffusion at the surface layers of the materials being joined. Solid-state diffusion bonding is a process by which two adjacent interfaces can be joined at an elevated temperature (about 50 to 90% of the absolute melting point of the parent material) using an applied pressure for a time ranging from a few minutes to a few hours. Joining of dissimilar materials with different thermo-physical characteristics, which is generally not possible by other processes, may be achieved by diffusion bonding. Diffusion bonding can provide a solid state diffusion bond that forms a hermetic seal between the two components. Diffusion bonding can also eliminate gold or metal brazing material from the joint area and thus can reduce the overall processing temperature exerted on the assembled components. In addition, a diffusion bond can reduce the separation distance between the joined components.

To facilitate diffusion bonding, the joint area of ceramic portion 24 may be coated with a metallization layer via sputtering. The metallization material may include, for example, niobium, rhodium, hafnium, tantalum, titanium, platinum or combinations thereof. In preferred embodiments, the metallization material may include niobium, platinum, titanium, or combinations thereof, and more preferably may include niobium. The metallization layer can have any useful thickness. In some embodiments, the metallization layer may have a thickness of less than 3 micrometers or is in a range from about 10 nanometers to about 1 micrometer.

Once coated, ceramic portion 24 and intermediate metal ring 40 may be aligned with one another and compressed together under a pressure of about 1-5 MPa. The parts may then be heated in a hot press at a temperature of about 800 to 1000 degrees centigrade or in a range from 850 to 950 degrees centigrade under vacuum (e.g., about 10-6 Torr) or an inert atmosphere. These temperatures are less than the melting point of gold, for example and thus may exert less thermal stress on ceramic portion 24, metal ring 40, and case portion 26 than that exerted during brazing.

In some embodiments, the braze or diffusion bond formed between intermediate metal ring 40 and ceramic portion 24 may be substantially nickel free. In some examples, the resultant joint may contain less than 5 wt. % nickel, less than 1 wt. % nickel, and more preferably does not contain nickel. In some embodiments, the braze or diffusion bond formed between intermediate metal ring 40 and ceramic portion 24 may be characterized by the amount of leachable nickel material within the joint. For example, the extractable nickel content from IPG 12 may be evaluated using standardized test method in accordance with ISO 10993. IPG 12 may be placed in a solution soak using inductively coupled plasma (ICP) and the solution evaluated for nickel content as a function of time. In preferred examples, the leachable nickel content is less than 300 μg/day in accordance with current EPA standards, more preferably less than 100 μg/day, and even more preferably below detectable limits. In preferred embodiments, the braze or diffusion bond formed between metal ring 40 and ceramic portion 24 may be substantially free of nickel such that it contains less than 5 wt. % nickel according to the starting braze materials, less than 1 wt. % nickel, and even more preferably is nickel free.

Figure 5:
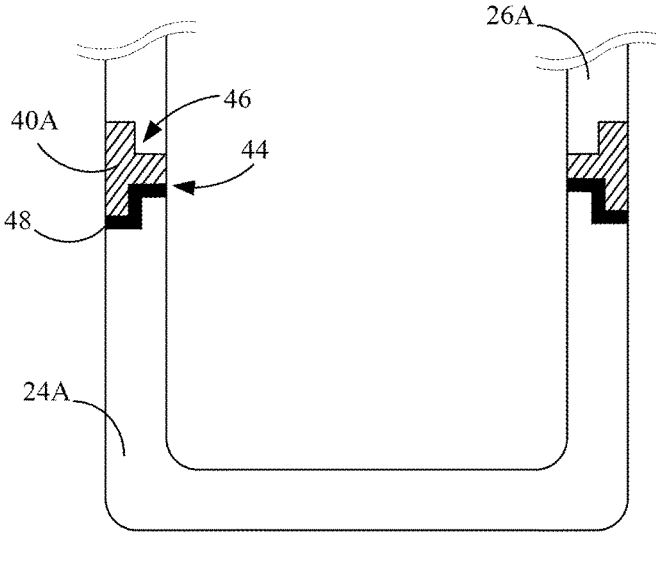
FIG. 5 is a cross-sectional view of a joint formed between a ceramic portion, intermediate metal ring, and case portion.
Figure 6A:
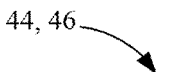
FIGS. 6A-6C show additional example shape configurations that can be used with mechanical alignment guides between a ceramic portion, an intermediate metal ring, and a case portion.
Figure 6A:
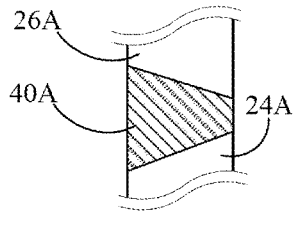
Figure 6B:
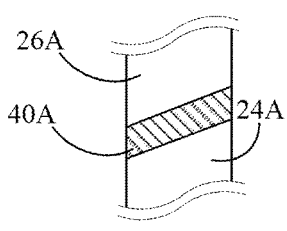
Figure 6C:
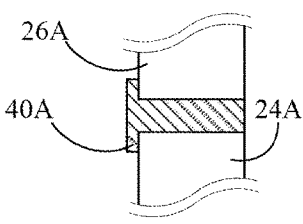

In some embodiments, one or more of ceramic portion 24, intermediate metal ring 40, or case portion 26 may define one or more mechanical alignment guides. For example, FIG. 5 provides a cross-sectional view (e.g., along line A-A of FIG. 4B) of a joint formed between ceramic portion 24A, intermediate metal ring 40A, and case portion 26A. As shown in FIG. 5, each of ceramic portion 24A, intermediate metal ring 40A, or case portion 26A define alignment guides 44 and 46 that mechanically interlock to help align the respective components with one another during assembly. Alignment guides 44 and 46 may be configured using any suitable shape, quantity, or other design feature. In some embodiments, mechanical alignment guides 44 and 46 may resemble adjacent shiplap joints as shown in FIG. 5. Additionally or alternatively, mechanical alignment guides 44 and 46 may be a simple taper so that the two components seat together, overlapping edges, more complex geometrical shapes, or combinations thereof. FIGS. 6A-6C show additional example shape configurations that can be used with mechanical alignment guides 44 and 46. While FIG. 5 shows mechanical alignment guides 44 present on both ceramic portion 24A and intermediate metal ring 40A and alignment guides 46 present on both case portion 26A and intermediate metal ring 40A, such guides need not be present on each component and may be present on only one component (e.g., intermediate metal ring 40A) or present at only one joint (e.g., between intermediate metal ring 40A and either ceramic portion 24A or case portion 26A).

While case portion 26 is described primarily as a metal, in other embodiments, case portion 26 may be formed using another material. For example, in some embodiments case portion 26 may be formed of a ceramic material which may be the same or different from ceramic portion 24. Forming case portion 26 from a ceramic material may provide advantages with regulating the temperature of the device. Additionally, or alternatively, by constructing the case portion 26 using a ceramic material, the recharge coil 32 may be repositioned or enlarged within IPG 12 (e.g., wrapped around the perimeter of circuit board 34 as described above with respect to FIG. 3) to improve the recharge efficiency in the device by increasing the coil length and coil aperture size. In such examples, case portion 26 may be joined to ceramic portion 24 using intermediate metal ring 40 and braze or diffusion bonding techniques like those disclosed above.

Figure 2C:
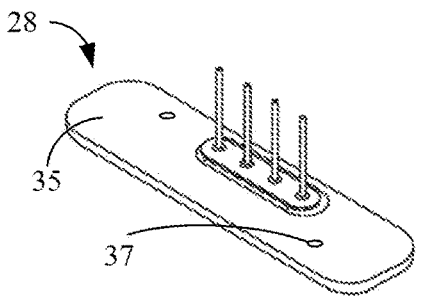

Referring to FIGS. 1 and 2A-2C, IPG 12 also includes header portion 22 configured to electrically couple to the implantable neurostimulation lead 14. Header portion 22 includes a connection port 13 that receives a proximal end of lead 14 and a connector stack 30 that electrically couples to lead 14 to provide electrical communication with neurostimulation electrodes 18. In preferred embodiments, header portion 12 may be joined to case portion 26 using multi-pin feed-through assembly 28 that couples with the connector stack 30. FIG. 2C is a schematic view of example multi-pin feed-through assembly 28. The multi-pin feed-through assembly 28 may be prefabricated, such as those available from Morgan Advanced Materials, to help provide versatility in the assembly of IPG 12. Feed-through assembly 28 may include a metallic base plate 35 (e.g., an alumina ceramic plate along with a titanium alloy flange) that may be used to bond header portion 22 to case portion 26. In embodiments where case portion 26 is metal, base plate 35 may be laser welded to case portion 26 to provide a hermetic seal. Optionally, base plate 35 may be configured to include alignment guides 37 (e.g., alignment pins or alignment apertures) configured to facilitate proper alignment between header portion 22 and circuit board 34, case portion 26, or both.

In some embodiments, a Balseal® connector block may be used as connector stack 30 that is electrically connected to four platinum/iridium alloy feed-through pins which are brazed using gold to an alumina ceramic plate along with a titanium alloy flange. In some embodiments, feed-through assembly 28 may be laser seam welded to a titanium case portion 26 to form a hermetic housing for the electronics, which complete hermetic housing can define a sealed internal volume. In other embodiments in which case portion 26 includes ceramic material, metallic base plate 35 may be brazed or diffusion bonded to case portion 26 using techniques similar to those described above.

IPG 12 may include additional components useful for the operation of IPG 12. The components forming the electronic circuitry for IPG 12 can be embodied in hardware, software, or both and can be located, at least partially, within the hermetically sealed internal housing volume of IPG 12. Each of the electrical components can be implemented using the processor, memory, or other hardware component in IPG 12.

In some embodiments, IPG 12 can include a communication module configured to send data to and receive data from other components, devices, and the like of nerve stimulation system 10 including, but not limited to, the clinician programmer or remote. In some embodiments, the communication module may be configured to work with charging coil 32 or antenna 39 to send information to and receive information from one or several of the other components associated with IPG 12.

Additionally, IPG 12 can include a data module configured to manage data relating to the identity and properties of IPG 12. The data module can include one or more databases containing information relating to IPG 12 such as, for example, data that identifies the device, data identifying functions, power consumption, charge capacity, or power storage capacity of IPG 12, data identifying potential recharge parameters, and the like.

IPG 12 can also include a pulse control module configured to control the generation of one or several pulses by IPG 12 for stimulation therapy including, but not limited to, pulse patterns, programs, or the like. Such information can identify the desired frequency, amplitude, and duration for therapy IPG 12 may also include a charging module configured to control the recharge cycle of IPG 12. In some embodiments, the charging module may communicate with an internal temperature sensor, humidity sensor, or both, mounted within the housing of IPG 12 to provide feedback or monitor the recharge process to ensure operation within desired safety parameters. In embodiments where IPG 12 includes a humidity sensor, the sensor may be used to monitor the integrity of the hermetic seal of the housing of IPG 12. If the seal is compromised, the humidity sensor may communicate via, for example, charging coil 32 or antenna 39 to an external device to indicate consultation with a physician or replacement of IPG 12 is needed.

The inclusion of ceramic portion 24 and other components of IPG 12 may allow the IPG to define a relatively small volume. In some embodiments, IPG 12 may have a total volume of less than 10 cubic centimeters (c.c.), and more preferably about 5 c.c.

Comparative Example 1

A Sacral Neurostimulator available from Axonics Modulation Technologies containing a ceramic and titanium case portion brazed together using a TiNi braze is placed within a beaker containing 250 mL of saline (e.g., Sodium Chloride 0.9% IV Injection Solution Viaflex 250 mL 250 ml/Bg available from Baxter Healthcare). The device is operated to deliver simulated neurostimulation using an Axonics neurostimulation lead connected to the neurostimulator. The device is operated for 24 hrs. The device is removed from the beaker and the saline solution is tested for nickel content. The observed nickel content will be greater than about 300 µg/day.

Example 1: Improved Sacral Neurostimulator

A Sacral Neurostimulator available from Axonics Modulation Technologies containing a ceramic and titanium case portion is disassembled by separating the ceramic and titanium case portions and mechanically removing the braze material between the ceramic and titanium case portions. An intermediate metal ring comprising Grade 4 Titanium is machine fabricated to mechanically align with the disassembled ceramic and titanium case portions. A joint interface of the ceramic case portion is sputtered with a layer of niobium metal. A layer of gold foil is placed over the niobium layer and the ceramic case portion and the intermediate metal ring are brought into direct contact. The components are heated to about 1100° C. allowing the gold to braze the metal ring to the ceramic portion. The joined part is cooled and the Sacral Neurostimulator is reassembled by laser welding the intermediate metal ring to the titanium case portion. The operations test described by Comparative Example 1 is carried out on the modified Sacral Neurostimulator. The device is removed from the beaker and the saline solution is tested for nickel content. The observed nickel content will be less than 300 µg/day.

Example 2: Improved Sacral Neurostimulator

A Sacral Neurostimulator available from Axonics Modulation Technologies containing a ceramic and titanium case portion is disassembled by separating the ceramic and titanium case portions and mechanically removing the braze material between the ceramic and titanium case portions. An intermediate metal ring comprising Grade 4 Titanium is machine fabricated to mechanically align with the disassembled ceramic and titanium case portions. A joint interface of the ceramic case portion is sputtered with a layer of niobium metal. The sputtered ceramic portion and intermediate metal ring are aligned and compressed together under a pressure of about 1-5 MPa and heated to 850 to 950° C. The joined part is cooled and the Sacral Neurostimulator is reassembled by laser welding the intermediate metal ring to the titanium case portion. The operations test described by Comparative Example 1 is carried out on the modified Sacral Neurostimulator. The device is removed from the beaker and the saline solution is tested for nickel content. The observed nickel content will be less than 300 µg/day.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable pulse generator configured for delivering one or more electrical pulses to a target region within a body of a patient, the implantable pulse generator comprising a hermetically sealed housing comprising:

a ceramic portion comprising a first ceramic material, the ceramic portion defining a first inner volume;

a case portion comprising a second ceramic material, the case portion defining a second inner volume;

an intermediate metal ring positioned between the ceramic portion and the case portion, wherein the intermediate metal ring comprises:

a first side joined to the ceramic portion by a first braze material or a first diffusion bond, wherein the first braze material or the first diffusion bond is substantially free of nickel, and a second side joined to the case portion by a second braze material or a second diffusion bond, wherein the second braze material or the second diffusion bond is substantially free of nickel, wherein the intermediate metal ring defines one or more first alignment guides on the first side configured to physically align the intermediate metal ring with the ceramic portion and one or more second alignment guides on the second side configured to physically align the case portion with the intermediate metal ring during assembly of the implantable pulse generator;

a header portion defining a third inner volume, the header portion being configured to electrically couple to an implantable neurostimulation lead, wherein the header portion comprises a feed-through assembly that connects the header portion to the case portion, and wherein the feed-through assembly electrically couples components of the header portion and the implantable neurostimulation lead to circuitry positioned within the second inner volume; and a charging-coil assembly comprising a charging coil, wherein the charging-coil assembly is at least partially housed within the first inner volume, wherein the charging-coil assembly is configured to receive wireless power through the first ceramic material from an external charging device to charge a battery at least partially positioned within the second inner volume, and wherein the charging coil extends at least partially around a perimeter of the circuitry positioned within the second inner volume.

2. The implantable pulse generator of claim 1, wherein the feed-through assembly comprises a multi-pin feed-through assembly comprising a metallic base plate, and wherein the metallic base plate is coupled to the case portion to create a hermetic seal.

3. The implantable pulse generator of claim 1, wherein the ceramic portion comprises zirconia or alumina.

4. The implantable pulse generator of claim 1, further comprising a humidity sensor configured to:

monitor an internal humidity within the hermetically sealed housing;

determine, based on the monitored internal humidity, that the hermetically sealed housing is compromised; and output an indication that a consultation with a physician or replacement of the implantable pulse generator is needed.

5. The implantable pulse generator of claim 1, wherein the intermediate metal ring comprises a titanium material ranging from Grade 1 Titanium to Grade 4 Titanium.

6. The implantable pulse generator of claim 1, wherein the ceramic portion is coated with a wetting agent comprising one or more of rhodium, hafnium, tantalum, titanium, and platinum, wherein the wetting agent is between the ceramic portion and the first braze material, wherein the wetting agent has a thickness in the range of about 1 to 3 micrometers.

7. A method of assembling an implantable pulse generator configured to deliver one or more electrical pulses to a target region within a body of a patient via an implantable neurostimulation lead, the method comprising:

forming a ceramic portion comprising a first ceramic material, the ceramic portion defining a first inner volume;

aligning the ceramic portion adjacent to a first side of an intermediate metal ring, wherein the intermediate metal ring comprises a different material than Grade 5 Titanium, and joining the ceramic portion to the first side of the intermediate metal ring by brazing or diffusion bonding, wherein a braze material of the brazing or a diffusion bond of the diffusion bonding is substantially free of nickel and forms a first hermetic seal between the ceramic portion and the intermediate metal ring;

depositing at least a portion of a charging-coil assembly within the first inner volume, wherein the charging-coil assembly comprises a charging coil, and wherein the charging-coil assembly is configured to receive wireless power through the ceramic material from an external charger to charge a battery at least partially housed within a second inner volume defined by a case portion, wherein the case portion comprises a second ceramic material, wherein the charging coil extends at least partially into the second inner volume; and joining a second side of the intermediate metal ring to the case portion to form a second hermetic seal, wherein the intermediate metal ring defines one or more first alignment guides on the first side configured to physically align the intermediate metal ring with the ceramic portion and one or more second alignment guides on the second side configured to physically align the intermediate metal ring with the case portion during assembly of the implantable pulse generator.

8. The method of claim 7, further comprising joining the case portion to a header portion to create a hermetically sealed housing, wherein the header portion comprises a multi-pin feed-through assembly comprising a metallic base plate, and wherein the metallic base plate is laser-welded, brazed, or diffusion-bonded to the case portion.

9. The method of claim 7, wherein joining the second side of the intermediate metal ring to the case portion comprises laser welding.

10. The method of claim 7, wherein joining the ceramic portion to the first side of the intermediate metal ring comprises brazing using a gold braze material.

11. The method of claim 10, further comprising sputtering a braze wetting agent comprising niobium on the ceramic portion prior to brazing.

12. An implantable neurostimulator device configured for delivering one or more electrical pulses to a target region within a body of a patient via an implantable neurostimulation lead comprising a plurality of neurostimulation electrodes electrically coupleable to the implantable neurostimulator device, the implantable neurostimulator device comprising:

a ceramic portion comprising a first ceramic material and forming a first part of a housing of the implantable neurostimulator device, wherein the ceramic portion defines a first inner volume;

a case portion comprising a second ceramic material, the case portion forming a second part of the housing of the implantable neurostimulator device, wherein the case portion defines a second inner volume;

an intermediate metal ring comprising a different material than Grade 5 Titanium, the intermediate metal ring being positioned between the ceramic portion and the case portion and forming a third part of the housing of the implantable neurostimulator device, wherein the intermediate metal ring comprises a first side joined to the ceramic portion by a first braze material or a first diffusion bond, wherein the first braze material or the first diffusion bond is substantially free of nickel, wherein the intermediate metal ring comprises a second side joined to the case portion by a laser-weld joint or by a second braze material or a second diffusion bond, wherein the second braze material or the second diffusion bond is substantially free of nickel, and wherein the ceramic portion, the case portion, and the intermediate metal ring collectively define a third inner volume of the housing, and wherein the intermediate metal ring defines one or more first alignment guides with the first part of the housing configured to physically align the intermediate metal ring with the ceramic portion and one or more second alignment guides with the second part of the housing configured to physically align the intermediate metal ring with the case portion during assembly of the implantable pulse generator;

a header portion configured to electrically couple to the implantable neurostimulation lead, wherein the header portion comprises a multi-pin feed-through assembly comprising a metallic base plate, wherein the metallic base plate of the multi-pin feed-through assembly is laser-welded, brazed or diffusion bonded to the case portion to provide a hermetic seal between the header portion and the case portion, wherein the multi-pin feed-through assembly electrically couples components of the header portion and the implantable neurostimulation lead to electronic circuitry at least partially positioned within the second inner volume; and electronic circuitry disposed within the third inner volume of the housing, wherein the electronic circuitry is configured to generate the one or more electrical pulses delivered to the target region within the body of the patient via the implantable neurostimulation lead, wherein the electronic circuitry comprises:

a printed circuit board at least partially housed within the second inner volume, the printed circuit board having a rechargeable battery and a temperature sensor electrically coupled thereto, wherein the temperature sensor is configured to detect a temperature of the implantable neurostimulator device during a recharge cycle of the implantable neurostimulator device or while delivering the one or more electrical pulses; and a charging-coil assembly comprising a charging coil defining a central coil axis, wherein the charging-coil assembly is housed within the first inner volume so that the central coil axis is substantially parallel to a normal defined by a major plane of the implantable neurostimulator device, and wherein the charging-coil assembly is configured to receive wireless power through the ceramic material from an external charging device to charge the rechargeable battery;

wherein the implantable neurostimulator device is hermetically sealed and defines a total volume of less than 10 cubic centimeters, and wherein the charging coil extends at least partially around a perimeter of the printed circuit board positioned within the second inner volume.

13. The implantable neurostimulator device of claim 12, wherein the implantable neurostimulator device has a leachable nickel content of less than about 300 micrograms per day ($\mu$g/day).

14. The implantable neurostimulator device of claim 12, wherein the metallic base plate of the multi-pin feed-through assembly comprises at least two alignment guides configured to physically align the multi-pin feed-through assembly with the printed circuit board or the case portion during assembly of the implantable neurostimulator device.

15. The implantable neurostimulator device of claim 14, wherein the at least two alignment guides of the metallic base plate comprise at least two alignment apertures defined by the metallic base plate.

\* \* \* \* \*